(12) United States Patent
Selby et al.

(10) Patent No.: US 10,195,634 B2
(45) Date of Patent: Feb. 5, 2019

(54) SEPARABLE MEMBRANE IMPROVEMENTS

(71) Applicant: The Technology Partnership PLC, Royston, Hertfordshire (GB)

(72) Inventors: Robert Gordon Maurice Selby, Melbourn (GB); Daniel Geoffrey Tyler Strange, Cambridge (GB)

(73) Assignee: The Technology Partnership PLC (GB)

(*) Notice: Subject to any disclaimer, the term of this patent is extended or adjusted under 35 U.S.C. 154(b) by 381 days.

(21) Appl. No.: 14/903,753

(22) PCT Filed: Jul. 9, 2014

(86) PCT No.: PCT/GB2014/052084
§ 371 (c)(1),
(2) Date: Jan. 8, 2016

(87) PCT Pub. No.: WO2015/004449
PCT Pub. Date: Jan. 15, 2015

(65) Prior Publication Data
US 2016/0158789 A1 Jun. 9, 2016

(30) Foreign Application Priority Data
Jul. 9, 2013 (GB) .................................. 1312263.5

(51) Int. Cl.
*B05B 17/06* (2006.01)
*B05B 17/00* (2006.01)
(Continued)

(52) U.S. Cl.
CPC ....... *B05B 17/0646* (2013.01); *A61M 11/005* (2013.01); *B05B 1/14* (2013.01);
(Continued)

(58) Field of Classification Search
CPC ... B05B 7/2408; B05B 17/06; B05B 17/0607; B05B 17/0646; B05B 1/14; B05B 1/185; A61M 11/005
(Continued)

(56) References Cited

U.S. PATENT DOCUMENTS 3,561,444 A 2/1971 Boucher
3,812,854 A 5/1974 Michaels et al.
(Continued)

FOREIGN PATENT DOCUMENTS

CA 2162399 A1 12/1994
EP 0431992 A1 6/1991
(Continued)

OTHER PUBLICATIONS

International Search Report and Written Opinion for Application No. PCT/GB2014/052084 dated Dec. 12, 2014.

*Primary Examiner* — Steven J Ganey
(74) *Attorney, Agent, or Firm* — Lerner, David, Littenberg, Krumholz & Mentlik, LLP

(57) ABSTRACT

An apparatus is provided for nebulizing a liquid from a liquid supply through a membrane comprising first and second surfaces and a plurality of apertures extending through the membrane. The apparatus includes an area for receiving a liquid supply, arranged to deliver a liquid to the first surface of the membrane, a vibrator member, arranged to vibrate the membrane to eject liquid droplets from the front surface of the membrane on vibration; and a mechanical coupling mechanism, arranged to provide a removable mechanical clamping force for clamping the membrane to the vibrator member. Various mechanisms for implementing the mechanical coupling are provided, and liquid containers and membranes for use in the device are proposed.

22 Claims, 10 Drawing Sheets

(51) Int. Cl.
  *B05B 7/24* (2006.01)
  *B05B 1/18* (2006.01)
  *B05B 1/14* (2006.01)
  *A61M 11/00* (2006.01)

(52) U.S. Cl.
  CPC ............ *B05B 1/185* (2013.01); *B05B 7/2408* (2013.01); *B05B 17/06* (2013.01); *B05B 17/0607* (2013.01)

(58) Field of Classification Search
  USPC .................. 239/102.1, 102.2, 302, 552, 600; 128/200.14, 200.16
  See application file for complete search history.

(56) References Cited

U.S. PATENT DOCUMENTS

| | | | |
|---|---|---|---|
| 4,533,082 A | 8/1985 | Maehara et al. | |
| 4,702,418 A | 10/1987 | Carter et al. | |
| 5,486,550 A | 1/1996 | Lubas | |
| 5,518,179 A | 5/1996 | Humberstone et al. | |
| 5,838,350 A | 11/1998 | Newcombe et al. | |
| 6,629,646 B1 * | 10/2003 | Ivri | A61M 11/005 239/102.2 |
| 8,870,090 B2 * | 10/2014 | Feriani | B05B 17/0684 239/102.2 |
| 2008/0111003 A1 | 5/2008 | Yu et al. | |
| 2010/0219263 A1 | 9/2010 | Feriani et al. | |
| 2010/0313883 A1 | 12/2010 | Von Hollen et al. | |
| 2011/0139150 A1 | 6/2011 | Gallem et al. | |
| 2011/0203580 A1 | 8/2011 | Papania et al. | |

FOREIGN PATENT DOCUMENTS

| | | |
|---|---|---|
| EP | 1475108 A2 | 11/2004 |
| EP | 1559436 A1 | 8/2005 |
| TW | 201242627 A | 11/2012 |
| WO | 9310910 A1 | 6/1993 |
| WO | 9422592 A1 | 10/1994 |
| WO | 2006006963 A2 | 1/2006 |
| WO | 2008106616 A2 | 9/2008 |
| WO | 2009136304 A2 | 11/2009 |
| WO | 2009150619 A | 12/2009 |
| WO | 2010026532 A1 | 3/2010 |
| WO | 2011083380 A1 | 7/2011 |
| WO | 2012041938 A2 | 4/2012 |
| WO | 2012062619 A1 | 5/2012 |
| WO | 2012156724 A2 | 11/2012 |
| WO | 2012156725 A1 | 11/2012 |

* cited by examiner

SEPARABLE MEMBRANE IMPROVEMENTS

CROSS REFERENCE TO RELATED APPLICATIONS

The present application is a national phase entry under 35 U.S.C. § 371 of International Application No. PCT/GB2014/052084 filed on Jul. 9, 2014, published in English, which claims priority from United Kingdom Patent Application No. 1312263.5 filed on Jul. 9, 2013, all of which are incorporated herein by reference.

This invention relates to electronic spray devices in which a vibrating perforate membrane is used to generate liquid droplets; in particular, to how such devices can be made more useful by enabling the separation of the vibrating membrane from its driver element.

Electronic nebulisers that use ultrasonic vibration to generate liquid droplets are well known in the art and have found use in a wide range of fields including medical drug delivery and the treatment of air (for example fragrance delivery and humidification). A subset of such devices in widespread use (commonly referred to as 'pond misters') use a vibrating surface covered by liquid to cause droplets to be generated through the break-up of standing waves on the liquid free surface (U.S. Pat. No. 3,812,854 being an example). This break-up leads to droplets with a wide range of sizes being produced and shaping of the liquid container above the level of the liquid is used to limit the size range of droplets that escape and are delivered. With a wide range of droplets being contained and returned to the bulk liquid, such devices have low efficiency resulting in high power consumption. The efficiency of such devices can be improved by constraining the free surface of the liquid with a perforate membrane (U.S. Pat. No. 4,533,082 for example). This membrane may have just a single nozzle (for dispensing or printing applications for example in which individual drops may be dispensed on demand) or may have many thousand nozzles (for nebuliser applications for example). Relatively monodispersed droplets are produced when such perforate membranes are used in which the droplet diameter is related to the size of the openings, or nozzles, in the perforate membrane. Such devices still suffer multiple disadvantages: In particular, the vibrating surface needs to be mounted close to the membrane, but not touching, for effective droplet generation and not all liquid in the container can be delivered (as the liquid is required to transmit the pressure waves to the perforate membrane). A preferred embodiment of such devices is therefore one in which the perforate membrane itself is vibrated by the driver element (commonly called the actuator or vibrator element) with examples including U.S. Pat. No. 4,533,082 and EP 0431992. This enables the delivery of relatively well monodispersed droplets without requiring the pressure waves to be transmitted through a liquid layer further increasing efficiency and enabling a wider range of embodiments. A preferred embodiment of such a device such as described in U.S. Pat. No. 5,518,179 uses a bending mode actuator to deliver the vibrational energy to the membrane as this enables the use of thin low cost actuators and further increases efficiency.

Often it is desirable to use a master-cartridge model in which a master unit can spray liquid contained in a replaceable cartridge. Preferably, all liquid contacting components reside on the cartridge and as many non-liquid contacting components as possible reside on the master. This minimises the cost of the cartridge whilst avoiding liquid cross-contamination between cartridges and liquid contamination of the master. Examples of fields where such an approach finds use are the medical field and the consumer fragrance field. In the medical field dose sterility can be critical and this can be achieved by containing each dose in its own cartridge (or capsule). Also in the medical field the same master device may be designed to be used with more than one patient and cross-contamination should be avoided. In the fragrance field, each cartridge may contain a different fragrance and again cross-contamination should be avoided. Other fields in which similar requirements are met will be obvious to someone skilled in the art.

One approach to avoid cross contamination is to place the perforate membrane and actuator into the cartridge component with the electronics and power source in the master. This limits the required connection between the two components to electrical but, with the actuator in the cartridge, leaves a relatively high cost component in the cartridge. Further, and more importantly for medical applications where each cartridge contains a single dose, the cartridge size may be relatively large compared to the amount of liquid it contains. There is therefore a need to move the actuator out of the cartridge component leaving just the liquid contacting perforate membrane, as this approach can reduce both cartridge cost and size.

The requirement to avoid cross contamination is known in the art and, for relatively inefficient applications where low power consumption is not crucial, solutions have been proposed. U.S. Pat. No. 3,561,444 teaches, for a pond-mister style device, using a liquid that is not dispensed to provide the connection between the vibration element in the master and the surface to be vibrated in the cartridge. U.S. Pat. No. 4,702,418, WO 2006/006963, WO 2009/150619, WO 2010/026532 and WO 2009/136304 teach various means of connecting the vibration force to a surface in the cartridge that is situated in close proximity to a perforate membrane with the vibration then transmitted through the liquid to be sprayed. EP 1,475,108 and U.S. Pat. No. 5,838,350 teach of a piezoceramic component directly to a perforate membrane, but do not teach how this can be done in an efficient manner or without the connection approach resulting in excessive energy absorption. The Büchi B-90 Nano Spray Drier enables the perforate membrane to be replaced by requiring the user to screw the membrane onto the actuator using a custom nut to a specified torque level. Whilst this is suitable for a laboratory instrument the replacement process is hard to automate in a compact device it would not be acceptable for a device that is designed to be operated by a consumer for example.

Efficient connection of energy is even more critical for low power devices and in particular for devices where the actuator operates in bending mode, as in U.S. Pat. No. 5,518,179. Further, efficient connection of energy through a bending interface is significantly more challenging than efficient connection of energy through a translating interface. This is because a torque in addition to a normal force must be transmitted and also because any structures that result in the device becoming thicker (a screw thread for example) reduce vibration.

In summary, there is a requirement for a means to enable vibration to be effectively transmitted from an actuator to a perforate membrane in which the perforate membrane can be easily removed and replaced by a non-skilled consumer or automatically within a compact device. Such transmission would ideally not absorb excessive vibration energy. Such transmission would ideally not reduce the vibration amplitude of the perforate membrane. These preferable requirements are especially challenging with bending-mode actuator devices as they are more easily damped.

A magnetically attached membrane is disclosed in WO2012/156724. This uses a single magnetic circuit, created by a magnet or pair of magnets, to create an attractive force between an actuator and a separable perforate membrane.

This present invention relates to methods and devices for providing an attachment force via mechanical clamping means, avoiding the use of magnets, which can be expensive to manufacture and assemble, while also providing improved efficiency as compared to known mechanical solutions. Further advantages, such as improved manufacturability will also become apparent during the detailed description of the invention.

WO9422592 and WO9310910 disclose actuation mechanisms which enable aerosolisation with consistent droplet size and distribution. In each case, the actuator and a mesh are bonded to one another and, as such, once the device has been used, the sterility of the mesh is compromised.

Nebulisers are reusable systems that are used for treatments which require a number of repeated inhalations. These are generally cleaned after each use. Such a device is disclosed in CA20162399. This uses a mechanical hammer which squeezes the drug from a blister pack through nozzles to form a mist.

WO2008/106616 discloses a device which uses vibrations to deagglomerate and aerosolise a powder or other drug substance.

WO2012041938, US2010219263 and EP1559436 all make disclosures of devices in which successive doses of the substance to be dispensed use a common mesh or membrane, resulting in the risk of cross-contamination from one dose to the next, or the breading of bacteria on the mesh in between doses, which may lead to a risk of infection. A further risk of these devices is that nozzles may become blocked, which may lead to a reduced flow rate and therefore variable dose in between different uses of the device.

US2010313883 proposes a solution which claims to be low-cost, and which uses vibrations to create droplets without the use of a mesh. These types of solutions can result in poor control of the droplet size and hence measures are needed to filter large droplets for inhalation. The filtration disclosed therein relies on the aerodynamic separation of the droplets by size, which can be an imprecise filter, can vary strongly with airflow rate and thus also can give limited control of droplet sizes.

TW2012242627 has a mesh that is disposed of after each dose is dispensed by the device. However, in this instance, the vibrator element is also disposable with the mesh, which adds to the cost of the disposable portion of the device.

Potential drawbacks associated with known devices can therefore be as follows.

The sterility of a reusable mesh may be compromised as soon as the first dose is taken using the device.

Nebulising devices are generally used for a prolonged single period and then claimed by a user, which can result in potential cross contamination or in effective cleaning resulting in non-sterile conditions.

The residual dose that remains on a mesh after it has been actuated can cause a variation in the admitted dose on subsequent actuations due to blocking of nozzles of the mesh or membrane.

Where a vibrator element is disposed with the mesh or membrane, then this increases the cost of the disposable element.

WO2012062619 and US2011203580 each show possible ways in which the vibrator may be reusable yet the mesh or membrane used with the vibrator may be disposable. In these instances, the vibrations are transmitted through a liquid that is being nebulised. This can result in a complex arrangement and is potentially less effective or efficient, since the flow rate may be reduced, or the particle size potentially less closely controlled, due to variations in the properties of the fluid transmitting of vibrations. This can also be less power efficient due to the indirect coupling of the vibration and the damping properties of the fluid, especially in the case of air bubbles in the fluid.

U.S. Pat. No. 5,486,550 shows an alternative solution for re-using the vibrator with a disposable mesh or membrane. In this device, the vibrations are transmitted through a relatively large flange to which the mesh is attached. The flange is connected to the vibrator element. Because the mass of the vibrator part, including the flange, is relatively high, the natural frequency of the system is low. This can result in a less effective transition of vibration, particularly higher frequency vibrations. This can, in turn, decrease the achievable flow rate of droplets, whilst also increasing the cost, size, and the power consumption of the vibrator.

WO2011083380A1 describes the use of a magnetic coupling to temporarily attach a mesh or membrane to a vibration system. This can result in a relatively low cost, hygienic solution. However, long-term exposure of a permanent magnet to vibration and an alternating electronic field may risk degrading the magnet. Use of electromagnets in place of a permanent magnet risks increasing the cost of the resulting device significantly. Furthermore, the magnetic force can decrease greatly if the magnet and components are separated by only a small distance. Therefore, while the use of magnetic attachment can remove the need to clean the membrane by allowing replacement between uses, to provide good coupling between the mesh and the vibrating part the components should be in direct contact or be separated only by a high permeability material. Use of non-magnetic means of coupling therefore allows greater flexibility with regard to material selection for the mesh and fluid feed components. The present invention aims to overcome the drawbacks of the prior art, and provides an apparatus, for nebulising a liquid from a liquid supply through a membrane comprising first and second surfaces and a plurality of apertures extending the membrane from the first surface to the second surface, the apparatus comprising:

a liquid supply receiving area for receiving the liquid supply a vibrator member, arranged to vibrate the membrane to eject liquid droplets from the second surface of the membrane on vibration; and a mechanical coupling means, arranged to provide a removable mechanical clamping force for clamping the membrane to the vibrator member.

In the present invention, the provision of a mechanical coupling means, which is arranged to provide a removable mechanical clamping force for clamping the membrane to the vibrator member allows the removal and replacement of the membrane such that the vibrator member can be reused multiple times, while the membrane, and optionally a liquid supply, may be reused multiple times.

Typically the membrane and liquid supply will be a single replaceable unit to provide benefits not limited to one or more of dose metering, sterility between doses or ability to change formulation of droplet size and flow rate to suit the application. Different embodiments of a unit dose container can be integrated with the mesh forms for each of the embodiments. Unit dose containers which can be useful in such an application are disclosed in WO2012156725. The liquid supply could nonetheless be provided as a separate element or as a reservoir which is not integrated with the membrane. The liquid supply receiving area can therefore be arranged to receive a dose container, or to directly receive a liquid, to provide liquid to the first side of the membrane.

The vibrator member may comprise a vibrator element mounted to a substrate, which can allow for the provision of extra structural strength via the substrate and transmission of the vibrations from the vibrator element by the substrate to the membrane or another part of the apparatus.

The coupling means may be arranged to clamp the membrane directly to the vibrator member. This direct coupling can create a more direct transfer of vibrations to the membrane from the vibrator member, which can reduce the moving mass of the vibrating assembly, which includes the membrane, the vibrating element and any element connecting those two pieces. Therefore, reducing the member of elements between the vibrator member and the membrane can improve the transmission of vibration to the membrane. This can improve power efficiency and reliability of the vibrations and resulting droplets created by the apparatus.

The coupling means may be arranged to clamp the membrane directly to the vibrator element. Clamping directly to the vibrator element assists with even more direct transfer of vibrations to the membrane and thus improved efficiency of transfer of vibrations and droplet creation by vibration of the membrane.

The clamping forces of the coupling may be balanced within one or both of the vibrator member and the liquid supply. Where the clamping forces are balanced within the vibrator member itself, this can avoid vibrating forces being transferred between the vibrator member and other parts of the apparatus. Therefore, transmission of vibration from the vibrator to the membrane is not interfered with by forces and damping effects from the mass and/or elasticity of other parts of the apparatus.

In certain situations, the clamping force may be comprised in least in part by a reacting force from the liquid supply or a part of the liquid supply. By maintaining the clamping forces between the vibrator member and the liquid supply, vibrations are restricted to those elements and thus losses due to transmission of vibrations to or through other parts of the apparatus are minimised. This results in a more efficient device and can assist with creating with more consistent and controlled droplet sizes.

The reacting force that maintains the membrane in vibratory contact with the vibrator member may acts locally to the interface between the mesh and vibrator member. This can further assist in isolating the clamping forces from other parts of the apparatus whose mass and or elasticity may act to dampen vibrations and reduce efficiency. The arrangement can therefore result in a more efficient device.

The vibrator member may comprise first and second clamping regions, having a void therebetween, for allowing liquid pass through the membrane in the region of the void. This allows an essentially central part of the membrane to transmit fluid, while clamping occurs at substantially outer parts of the membrane, where optimal vibration transmission conditions may be obtained. This can also assist with general practical implementation of the device or apparatus.

The mechanical droplet means may be arranged to provide a clamping force substantially perpendicular to the plane of the membrane. Vibrations will generally be provided in a plane of the membrane and therefore providing a clamping force perpendicular to the plane of the membrane can avoid the vibrations in the plane of the membrane effecting the clamping force, which can result in more reliable and consistent transmission of vibrations to the membrane, while the clamping force can be set and/or controlled independently of the rate or amplitude of vibration.

At least a part of the clamping force may be provided by an interference fit between a membrane and the vibrator member.

At least a part of the clamping force may be provided by a resilient part of a flexible liquid supply, which may be a dose container.

At least a part of the clamping force may be provided by at least one flexible clamping member of the substrate. This consists of maintaining the clamping forces isolated within the substrate.

At least a part of the clamping force may be provided by a flexible part of the resilient membrane.

The flexible clamping member may comprise a membrane contact part and at least one flexible support for biasing the contact part towards the membrane.

A membrane for use with an apparatus with the present invention may comprise a clamping section arranged substantially perpendicular to the planar section of the membrane to receive a clamping force in a direction substantially perpendicular to the substantially planar section.

A membrane for use with an apparatus with the present invention may comprise a clamping section offset from the planar section of the membrane to receive a clamping force in a direction substantially perpendicular to the substantially planar section.

The clamping section may be substantially annular, for receiving a substantially radial clamping force from the coupling means.

The apparatus may be arranged for supporting the membrane to an outer lateral region of the membrane and the vibrator member may comprise a member in contact portion arranged to transmit vibration to the membrane at a point laterally inward from the outer lateral region. This allows mechanical contact with the vibrator member to be remote from a support portion of the membrane and can thus result in vibration of the membrane with minimal vibration of membrane supporting features, such as a mounting area or a liquid supply or dose container.

The membrane may therefore be supported at the outer lateral region by a membrane support member, which may be arranged for direct or indirect connection to the connector vibrator member, to provide the removable mechanical clamping force.

The portion of the membrane intended for vibration may have a substantially planar substantially circular form and a membrane contact portion of the vibrator member may be substantially circular.

The apparatus may be arranged to apply tension to the membrane via the membrane contact portion.

The membrane may be permanently attached to a dose container arranged for connection to the apparatus.

A dose container for the apparatus may be provided, comprising a container for carrying a dose of liquid, and opening for releasing the liquid from the container, a membrane located at the opening, the membrane comprising first and second surfaces and a plurality of apertures extending through the membrane from the first surface to the second surface for releasing liquid from the container through the apertures, and apparatus engaging means, for engaging the apparatus to locate the membrane at the membrane contact portion of the apparatus.

The vibration member of the apparatus may comprise at least one membrane engaging member arranged to engage at least one clamping portion of the membrane, such that rotational or translational movement of the membrane relative to the vibration membrane induces a clamping force of the membrane engaging member or members on the membrane. The clamping portion may be an opening in the membrane.

The membrane engaging member or members may protrude outwardly from a membrane mounting surface of the vibration member.

The membrane engaging member or members may protrude substantially diagonally with respect to the membrane mounting surface of the vibrating member.

The vibration member may comprise at least one guide portion for guiding a movement of the membrane relative to the membrane engaging member or members. This can ease installation of the membrane on the vibration member.

The guide portion may be substantially arcuate or circular, for guiding a rotational movement of the membrane. This can be particularly advantageous where a rotation of movement of the membrane is used to engage the membrane engaging members of the vibrator member.

A guide portion may be wholly or partially substantially linear or rectanguloid for guiding a translational movement of the membrane. Wholly or partially may apply to the arcuate or circular feature as well. The former can help with installation of the membrane when a substantially linear movement is used to engage a membrane with the membrane engaging member of members of the vibrator member.

In the guide portion may be an opening the vibration, or an edge of the vibration member, and the member engaging member or members may be arranged adjacent the opening.

The opening may be circular and the membrane engaging member or members may be arranged radially around the circular opening.

The opening may be substantially linear or rectanguloid and the engaging member or members may be arranged on one or both sides of the opening or edge.

A membrane may be provided for the apparatus of the invention, comprising a clamping region located adjacent the apertures of the membrane and at least one opening or edge arranged to engage the at least one membrane engaging member of the apparatus, to create a clamping force of the membrane engaging member or members on the membrane, via a rotational or translational movement of the membrane relative to the vibration member.

The vibration member of the apparatus may have a substantially planar form and the coupling means may comprise a substantially planar clamping plate, arranged to clamp the membrane to the vibrator member.

The vibrator member may have a substantially planar form and the coupling means may comprise a substantially planar clamping plate, arranged to clamp the membrane to the vibrator member.

At least one of the vibrator member and the clamping plate may comprise at least one indent or protrusion for aligning the membrane with the coupling means.

The vibrator member and the clamping plate may have a substantially disc-shaped form, with a substantially central opening for the passage of fluid through the apertures of the membrane when the membrane is clamped between the vibrator member and the clamping plate.

The vibrator member and the clamping plate have a substantially rectanguloid form, and are arranged adjacent an opening for the passage of fluid through the apertures of the membrane when the membrane is clamped between the vibrator member and the clamping plate.

The apparatus may comprise opposing sets of vibrator members and clamping plates arranged on substantially opposite sides of an opening for the passage of fluid through the apertures of the membrane when the membrane is clamped between the respective vibrator members and the clamping plates.

A membrane for an apparatus of the invention may comprise first and second surfaces and a plurality of apertures extending through the membrane from the first surface to the second surface, and further comprising at least one indent or protrusion corresponding to the indent or protrusion of the coupling means, for aligning the membrane with the coupling means.

The apparatus may be arranged to clamp the membrane between a clamping plate and the vibrator element. The vibrator element may be substantially hollow. The vibrator element may be arranged to receive a liquid supply comprising the membrane. The vibrator element may be substantially tubular, the clamping plate substantially annular and the membrane substantially circular.

A dose container may be provided for the apparatus of the invention, the dose container comprising:
  a container for carrying a dose of liquid;
  an opening for releasing the liquid from the container;
  a membrane located at the opening, the membrane comprising plurality of apertures extending through the membrane for releasing the liquid from the container;
  the membrane extending radially outwardly from the container in the plane of the membrane, such that the membrane can be clamped directly to the vibrator element of the apparatus.

The clamping means of the invention may comprise a resilient biasing member arranged to provide a resilient clamping force toward an outer edge of the first surface of the membrane, in opposition to a clamping force provided via the vibrator member, such that an outer edge of the membrane is clamped between the biasing member and the vibrator member.

The membrane may be substantially circular, the vibrator member may have a substantially circular central opening for the passage of fluid through the membrane and the biasing member may have a substantially circular form to apply the clamping force around the circular opening of the vibrator member.

The apparatus may further comprise a second resilient biasing member, arranged to provide a resilient clamping force in opposition to the clamping force of the first resilient biasing member, such that the vibrator member and the membrane are clamped together between the first and second resilient biasing members.

The first and/or second biasing member may be a disc spring, having a central opening for the passage of fluid through the membrane.

At least one of the biasing members is a disc spring having planar portion and an annular central section extending away from a planar portion to engage the membrane and/or the vibrator member.

The apparatus may further comprise a spacer member comprising a first spacer section for spacing outer edges of the disc springs apart by a first distance and a second, support section, for supporting the vibrator member at a set distance between the first and second disc springs Generally Applicable Actuator Design and Mounting The present invention is applicable to a wide range of actuator types but is of particular benefit to actuators that use a piezoelectric, electrostrictive or magnetostrictive material (i.e. a material that changes shape in response to an applied electric or magnetic field, henceforth referred to as the active component) in combination with a metal connection or support material (henceforth referred to as the passive component). Examples of such actuators include longitudinal actuators which drive the perforate membrane to vibrate in a direction generally parallel to the expansion and contraction direction of the active component, breathing mode actuators which drive the perforate membrane to vibrate in a direction generally normal to the expansion and contraction direction of the active component and bending mode actuators of the type described earlier and in more detail in U.S. Pat. No. 5,518,179, incorporated herein for reference, to which this invention is particularly applicable. Whilst for some actuators the passive layer does not itself deform and merely acts as a support component, for most actuator designs the passive layer itself expands, contracts, bends or deforms elastically in response to the deformation of the active layer. For example, for a longitudinal actuator the passive component can be used to amplify the strain rate of the active component and, for a bending mode actuator consisting of a unimorph, the passive component's characteristics heavily influence the actuator performance. For such actuators the passive layer material and design, herein referred to as a "deforming passive component", is integral to the actuator performance and modifying it or adding to its mass will impact the device performance.

For all such actuators a range of factors impact their performance. By performance, we mean their ability to cause the membrane to produce droplets whilst maximising the efficiency, minimising the size and minimising the cost of the overall system. Efficiency is here defined as the ideal energy required to produce the droplets divided by the energy into the system.

In relation to the actuator, particular features that improve performance are reducing actuator mass, reducing internal energy dissipation and reducing energy transmitted to components other than the perforate membrane as described in the following paragraphs:

Reducing actuator mass in general increases performance. This is because any mass needs to be accelerated requiring a force to be applied and increasing the stored energy. For a given quality factor (Q-factor), this leads to additional energy dissipation per vibration cycle. Other disadvantages of increasing actuator mass are an increase in actuator starting and stopping time and either increased complexity, increased cost or reduced efficiency of any drive circuitry, or a combination thereof.

Reducing internal energy absorption of the actuator (i.e. increasing its Q-factor) is important as this energy is dissipated as heat rather than being delivered to the membrane. Deformation of both the active and passive components of the actuator leads to thermal heating as does deformation of any bonding materials. For example, for a bending mode actuator the active and passive components are usually bonded together using an adhesive. Keeping this adhesive layer thin and rigid helps to avoid it absorbing excessive energy.

Reducing energy transmission from the actuator to parts other than the perforate membrane improves performance. This includes the liquid to be delivered as droplets (except in the vicinity of the membrane perforations). In general this can be accomplished by minimising the vibrational amplitude of the actuator (whilst maximising the vibrational amplitude of the membrane). Further, actuators usually need to be mounted to a support structure in order to operate as part of a device and for liquid to be reliably delivered to the perforate membrane. The design and implementation of this mounting can have a significant impact on the actuator performance and the amount of energy transmitted to the perforate membrane. A range of support structures are known in the art for different actuator types (long thin fingers and soft support rings being two such approaches) but in general they try to reduce the transmission of vibrational energy from the actuator to the mount. This can be more easily achieved when the mount does not need to support any large reaction forces that result from forces being applied to the actuator or perforate membrane elsewhere.

Generally Applicable Membrane Design and Actuator Attachment

To transmit energy efficiently from the actuator to the membrane requires careful design of the two components and their interaction. Aside from ensuring the components vibrate at the appropriate frequency and with the appropriate mode shape, a range of generally applicable features are required to deliver maximum membrane velocity for minimum energy consumption. This list of features is similar to what makes a good actuator but with some differences:

Firstly, the mass of the membrane should preferably be minimised especially any mass that does not stiffen the membrane. Minimising its mass reduces the force that must be supplied to it by the actuator reducing losses in that component. Any mass increases increase the required force that needs to be supplied requiring a larger, less efficient actuator.

Secondly, unless the membrane is separately supported (leading to reduced efficiency), the interface between the actuator and the membrane needs to transmit a periodic force oscillating about a mean of zero if gravity is neglected (i.e. the interface must support an instantaneous forces being applied in more than one direction). This may be push/pull, clockwise/anticlockwise torque, or similar.

Thirdly the energy absorbed in the interface between the actuator and the membrane should preferably be minimised. For devices which do not require the separation of the perforate membrane this can be achieved by several methods well known in the art. These include adhesive bonding, welding, brazing and soldering amongst others. All such means add minimal, if any, mass to the device, generally absorb little energy and do not reduce the amplitude of vibrations. They achieve these features by creating a very thin rigid bond directly between the two components. Bolting, clamping or screwing together the components is also used but, as previously discussed, this increases mass and can also impact the vibrational characteristics of the device.

Finally, energy transmitted to the liquid that does not go into the formation of droplets should preferably be minimised. This can be achieved by minimising any area of the membrane that is not perforate (i.e. by minimising areas of vibration that are liquid contacting but are not delivering droplets). Energy transmission to the liquid can also be reduced by using soft wicks or other similar means to deliver liquid rather than contacting the membrane with bulk liquid.

To summarise, any separable membrane design would ideally allow efficient transmission of energy from the actuator to the membrane in the form of an oscillating force about a mean of zero without absorbing energy. It would ideally minimise any mass increase of both the actuator and the membrane. It would ideally minimise any increased damping in the actuator. It would ideally minimise the energy transmitted by the actuator to elements other than the membrane (e.g. mount). It would ideally avoid transmitting energy to the liquid to be delivered.

PREFERRED EMBODIMENTS OF THE INVENTION

A removable mechanical clamping connection between the actuator and membrane has the ability to meet all of these preferred requirements. A range of aspects of the invention are now disclosed with reference to the following figures:

FIG. 1 summarises a range of actuator types and their interface to the perforate membrane for current, non-separable constructions;

Figure 1:
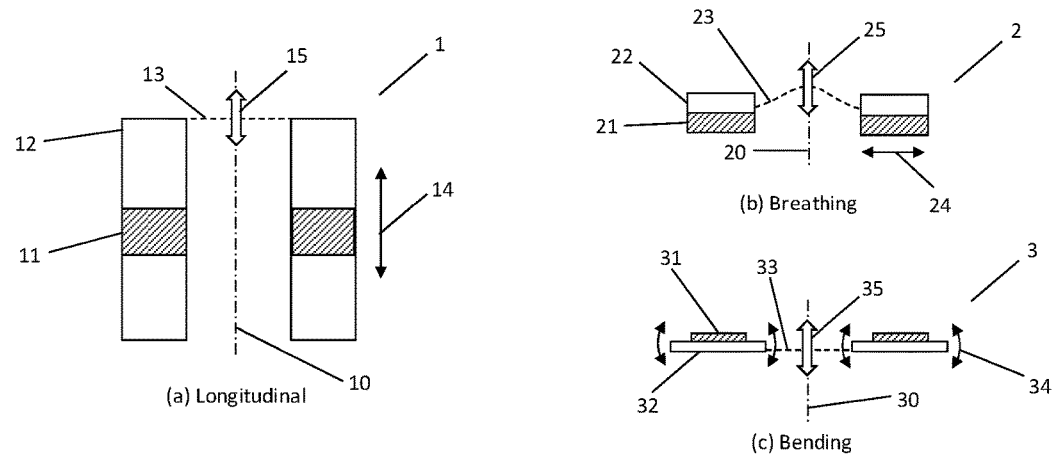
Figure 2:
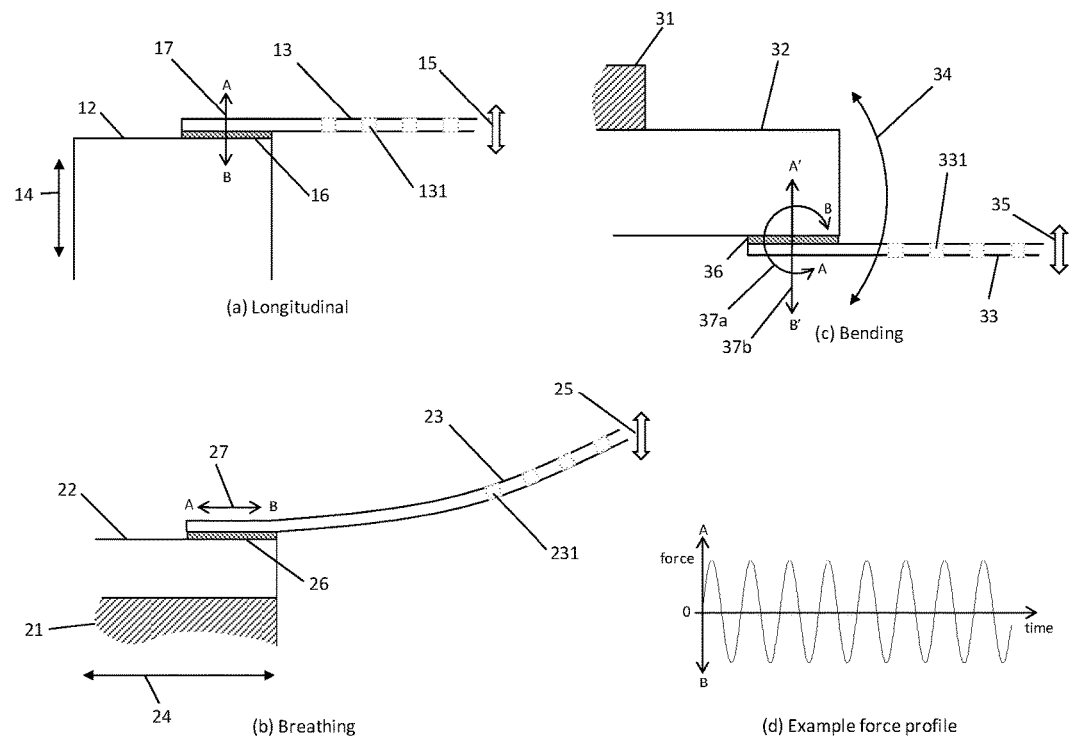
FIG. 2 is a detail view of the actuator to membrane interface showing the forces that need to be transmitted.
Figure 3:
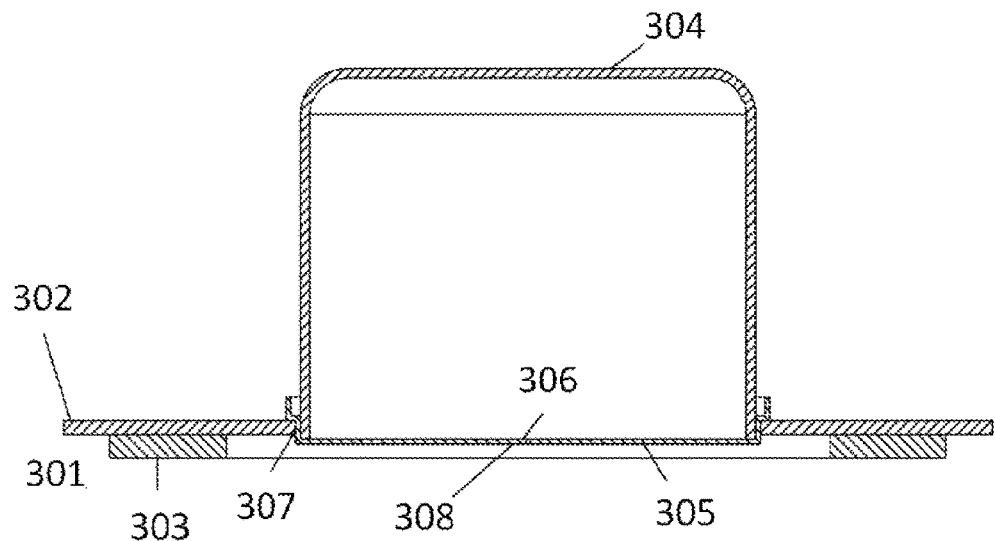
FIG. 3 shows a first embodiment of a vibrator member and membrane interface according to the present invention.
Figure 4A:
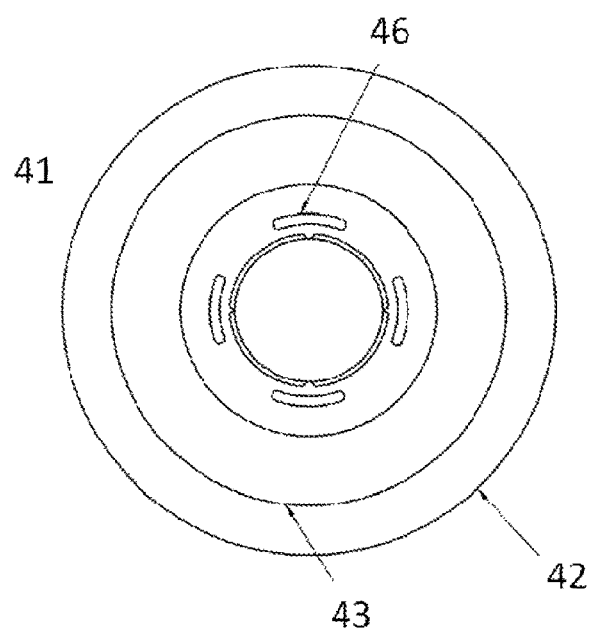
FIGS. 4A to 4E show further embodiments illustrating clamping means of the present invention.

FIG. 1(*a*) shows an axi-symmetric droplet production apparatus known in the art of the longitudinal type (1). The actuator consists of an active component (11) bonded to a deforming passive component (12) designed such that at resonance the passive component amplifies the strain of the active component. A perforate membrane (13) is bonded to the actuator and the device has an overall axis of symmetry (10). Expansion and contraction of the actuator (14) leads to amplified motion (15) of the perforate membrane in a generally parallel direction. The membrane itself may all vibrate in phase, have one wavelength of motion across its radius (i.e. the central region may be out of phase with the periphery), or more than one wavelength of motion, depending on the design. FIG. 2(*a*) shows the detail of the actuator to membrane interface for this apparatus. The membrane is permanently attached to the actuator through a means such as adhesive bonding, laser welding, brazing, soldering or similar (16). This attachment mechanism must transmit a time varying force (17) across the interface with the force primarily normal to the bonding surface in directions A and B. Such a force, be way of an example, is sketched in FIG. 2(*d*). When the force is in direction A the bond (16) is in compression and when the force is in direction B the bond is in tension.

FIG. 1(*b*) shows another axi-symmetric droplet production apparatus but of the breathing type. Again the actuator consists of an active (21) and passive (22) component but in this instance planar actuator motion (24) leads to vibration of the membrane (23) in a direction normal to the actuator motion (25). The bond interface is shown in FIG. 2(*b*). For this type of actuator the bond (26) must primarily support the transmission of a shearing force (27) in a time varying radially inwards and then radially outwards direction.

A third type of device to which this invention is applicable is shown in FIG. 1(*c*). This device uses a unimorph actuator comprising an active (31) and a deforming passive (32) layer that operates in bending (34). This bending motion is connected to the membrane (33) and drives the membrane to vibrate in a direction (35) normal to the unimorph neutral plane. The bond detail is shown in FIG. 2(*c*) and in this case the bond (36) must transmit a time varying torque (37*a*) and normal force (37*b*) from the actuator to the membrane. The relative intensities and phases of these two bulk forces will be design dependant but the result is that the bond must support radially and time varying shear, compression and tension across its surface. This bending mode actuator can be configured in an axi-symmetric geometry, wherein the dot-dash line (30) shows the axis of symmetry, or in linear format, where the dot-dash line (30) is the centre-line of an actuator that extends out of the page.

FIG. 3 illustrates an assembly 3 forming part of an apparatus of the present invention. The device includes a vibrator member 301 which comprises a substrate 302 and a vibrator element 303. A liquid supply means in the form of a dose container 304 is provided at a first side 306 of membrane 305 to deliver liquid to the first side 306 of the membrane. It can be seen in the figure that the membrane 305 comprises a clamping section 307, which is arranged substantially perpendicular to a central, planar, section of the membrane. It will be appreciated that the central, planar, section may be provided with a plurality of apertures extending through the membrane from the first surface 306 to a second surface 308 to allow a liquid within the liquid supply 304 to be delivered from the first side 306 to the second side 308 of the membrane. In this way, the liquid can be passed through the membrane by vibration of the vibrator member 301, which creates a series of droplets of a controlled size. In the illustrated embodiment, the liquid supply 304 and the vibrator member 301 have a substantially circular or annular form, as does membrane 306. However, a similar arrangement could be provided with substantially rectanguloid forms of the membrane, vibrator member and liquid supply 304, as could other forms, such as ovals and other substantially curved or rounded-corned shapes. A circular form can however be preferable, as it can help to ensure even distribution of clamping forces round the clamping section 307 of the membrane 305.

As can be seen in the figure, the clamping forces in the embodiment of FIG. 3 are substantially parallel to the plane of the membrane 305, and they act on the clamping section 307 of the membrane, which is arranged substantially perpendicular to the plane of the membrane.

FIG. 4A illustrates an alternative arrangement for providing clamping forces in a direction substantially parallel to the plane of the membrane, similar to the forces illustrated in FIG. 3. In both FIGS. 3 and 4, an interference fit is provided between at least a part of the membrane and the vibrator member. In FIG. 3, the interference fit is provided substantially entirely around the circumference of the membrane and the inner opening of the vibrator member. FIG. 4 illustrates an alternative embodiment, in which the interference fit is provided at a series of points around the circumference of an inner opening of the vibrator member. The points are illustrated as having a small area of contact, but a series of larger points may be provided having a substantially arcuate area of contact. FIG. 4A illustrates the vibrator member 41 having a substrate 42 and a vibrator element 43 mounted thereto. The vibrator member 41 is provided with an array of flexible clamping members 43, which comprise a first part for contacting the membrane and a second part which is a flexible support for biasing the contact part towards the membrane. The illustrated features can be provided in the vibrator member by processes such as laser cutting, etching or by stamping cut-outs, to create resilient members and membrane contacts regions in the vibrator member, preferably in the substrate 42.

Figure 4B:
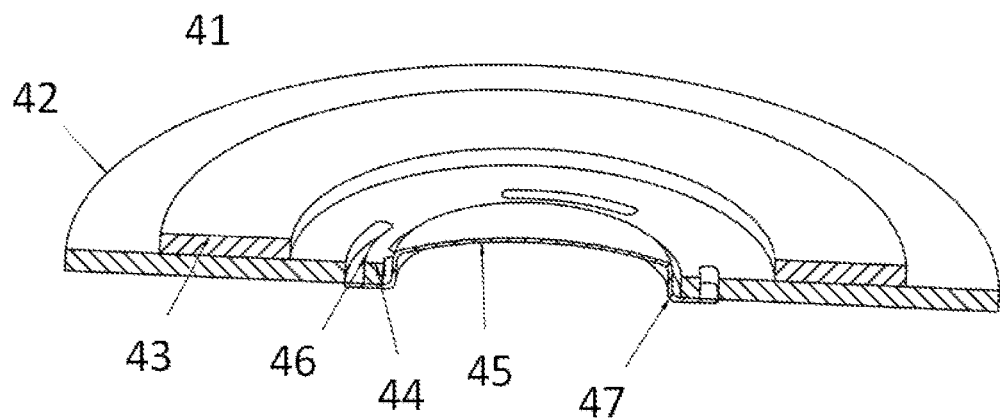
Figure 4C:
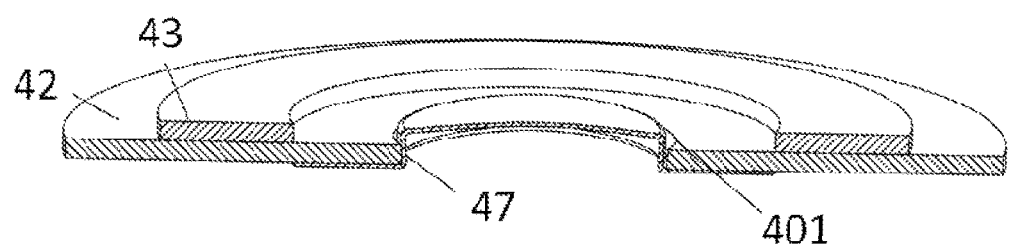
Figure 4D:
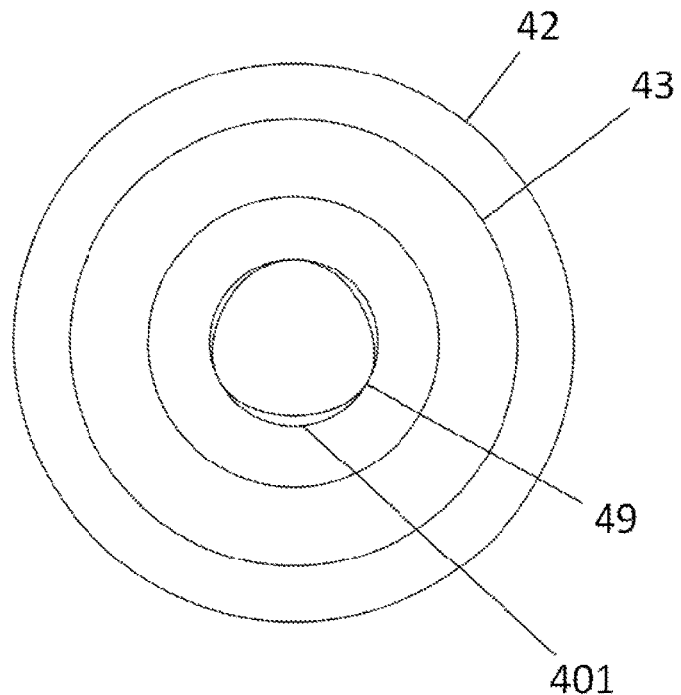
Figure 4E:
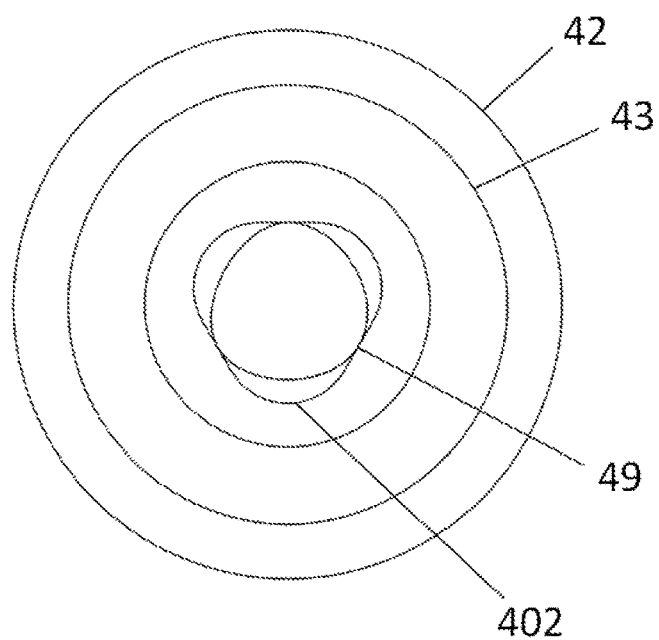

FIG. 4B shows a section through the arrangement of FIG. 4A, in which further detail of the flexible clamping members 43 of FIG. 4A can be seen. A clamping member comprises a member having a contact part 44, which is applied to a flexible support 46, such that the flexible support 46 biases the contact part 44 towards the membrane 45. The membrane has a clamping part 47 which is substantially perpendicular to the plane of a planar part of the membrane, in which the apertures for passage of liquid are provided. It is also possible to provide an alternative arrangement in which flexible clamping members are provided in the outer part of the membrane which contacts the substrate. In this way, a membrane can be provided comprising a vibration member contact portion and a flexible support, so that the vibration member can be simply constructed while the flexible portion is provided in the membrane in a manner such as that illustrated in FIG. 4C. The flexibility provided by the supports 46 as shown in 4A would, in this alternative arrangement, be provided in the inner membrane 47. By making the contact surface 47 non-circular, such as by use of a convex triangular form as illustrated in FIG. 4D, or by discrete radial protrusions, a degree of flexibility can be provided, which can allow for adaption for manufacturing tolerances and provide the sprung contact to couple vibration from the vibrator member to the mesh. An alternative implementation can be achieved if the surfaces 47 and 401 are shaped so that relative rotation between the two components allows locking of the two components. This can be achieved if both surfaces are shapes such as convex triangular profiles, as shown in exaggerated form on FIG. 4E, or have a degree of ovalisation, or similar, such that relative rotation brings the maximum radial dimensions of the mesh 49 into contact with a parts of the substrate inner surface 402, having a radial dimension less than the maximum radial dimension.

Figure 5A:
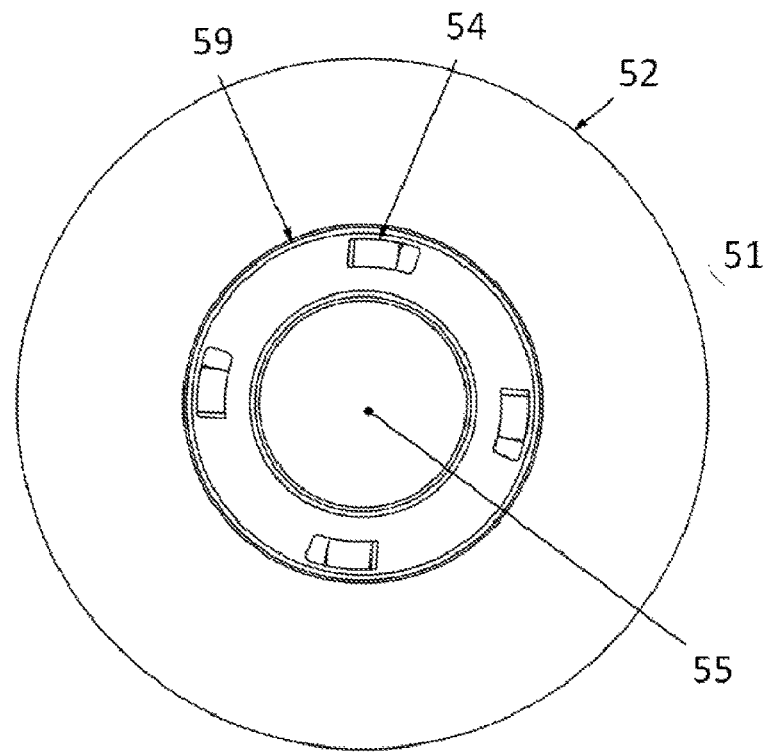
FIGS. 5A and 5B illustrate a further embodiment of a vibrator member-membrane clamping means of the present invention.

FIG. 5A shows a further alternative arrangement, in which a vibrator member 51, comprising a substrate 52 and a vibrator element 53, is provided with one or more membrane engaging members 54. The membrane engaging members of the illustrated embodiment comprise inclined portions of the substrate 42 which are arranged at a non-zero angle to the substrate, such that they project upwards from the substrate 52, away from its plane. It is thus possible to engage a portion of the membrane 45 between the membrane engaging member and a substantially planar membrane mounting surface of 56 of the substrate 52. Further advancing of the membrane between the membrane engaging member and the planar portion of the substrate induces a clamping force of the membrane engaging member or members on the membrane. In the illustrated embodiment, shown in FIGS. 5A and 5B, the membrane and vibrator member have a substantially circular form. In the illustrated embodiment, a rotational movement of the membrane relative to the vibration member induces a clamping force of the membrane engaging member on the membrane. However, it will be appreciated that a translational movement of the membrane relative to the vibration member could induce a similar clamping force of the membrane engaging member on the membrane. A simple linear translation could be used to bring the membrane between the engaging member and the vibrator member to create the clamping force. In the illustrated embodiment, the membrane engaging members are formed integrally with the vibrator member and protrude outwardly from a membrane mounting surface of 56 of the vibrator member, but they could also be applied as separate parts being attached to the vibrator member.

Figure 5B:
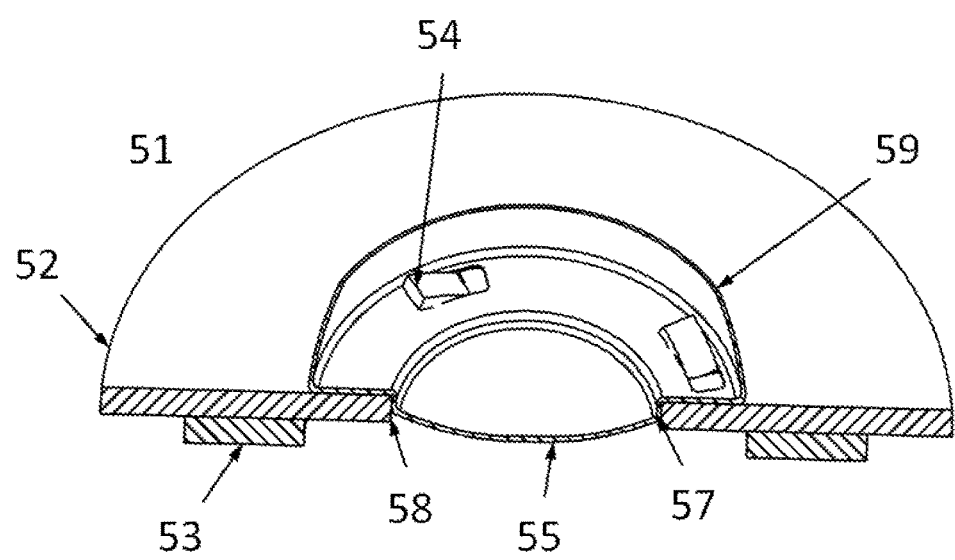

FIG. 5B shows a perspective view of the arrangement of FIG. 5A, in which further detail of the arrangement can be seen for clarity. It can be seen that the membrane engaging members 54 protrude outwardly and substantially diagonally with respect to the membrane mounting surface 56 of the vibrator member. However, other forms may be envisaged, such as substantially L-shaped portions.

The membrane 55 comprises a guide portion 57, which is configured to engage a corresponding guide portion 58 of the vibrator member. This is for guiding a movement of the membrane relative to the vibrator member to enable effective engagement of the membrane with the membrane engaging members 54 of the vibrator member 51. In the illustrated embodiment, the guide portion 58 is substantially circular for guiding a rotational movement of the membrane relative to the vibrator member. It will, however, be appreciated that a substantially linear guide portion 58 might be created in the vibrator member to guide a linear movement of the membrane relative to the vibrator member 51 to permit engagement of the membrane with membrane engaging members 54.

The guide portion 58 can be either an opening or an edge of the vibration member 51. The membrane engaging member or members may be arranged adjacent the opening or edge of the vibrator member to effectively guide the movement of the membrane in the region of the membrane engaging members. As in the illustrated embodiment, the opening which provides the guide portion 58 may be circular and the membrane engaging members 54 may be arranged radially around the opening.

A membrane for use in the embodiment of FIGS. 5A and 5B may be provided with at least one opening or edge, arranged to engage the at least one membrane engaging member 54 of the vibrator member, to create a clamping force of the membrane engaging member or members on the membrane by the rotational or translational movement of the membrane relative to the vibration member. The membrane may further comprise a guide portion for engaging a guide portion 58, numbered 57 in the figure.

The features for creating the membrane engaging members may be punched into the vibrator member, preferably the substrate, and may form a multi-start screw thread, or a "bayonet"-style mount. These may thus engage with holes or slots, or an edge of the membrane. The holes, slots or other engaging features of the membrane can be formed by low cost forming processes such as punching or etching. The membrane may have a 'return' feature, arranged substantially perpendicular to the plane of the membrane, to facilitate handling of the membrane and its engagement with the vibrator member and its membrane engaging members.

Other guide features may be provided on the membrane or on the vibrator member, in the form of bumps, small domes, protrusions or indentations, arranged substantially in the region of the holes in the membrane, or near the other engaging features of the membrane. This can allow a resilient or sprung clamping force to be generated to further improve the clamping force between the membrane and the vibrator member. The guide member of the membrane may be a substantially circular protrusion, or a 'spigot' feature, formed into the membrane as shown in FIG. 5B, which can allow the mesh to centre or substantially align on the vibrator member to align the prospective engaging portions of the vibrator member and the membrane. These features all allow the membrane to be repeatedly replaced and the vibrator member to be reused, with minimal additional components, and minimisation of vibrating mass, which can improve transmission of vibrations from vibrator member to membrane. The forming processes used to make the components can be efficient and low cost, without the need to use adhesives for bonding the membrane to the substrate.

Figure 6A:
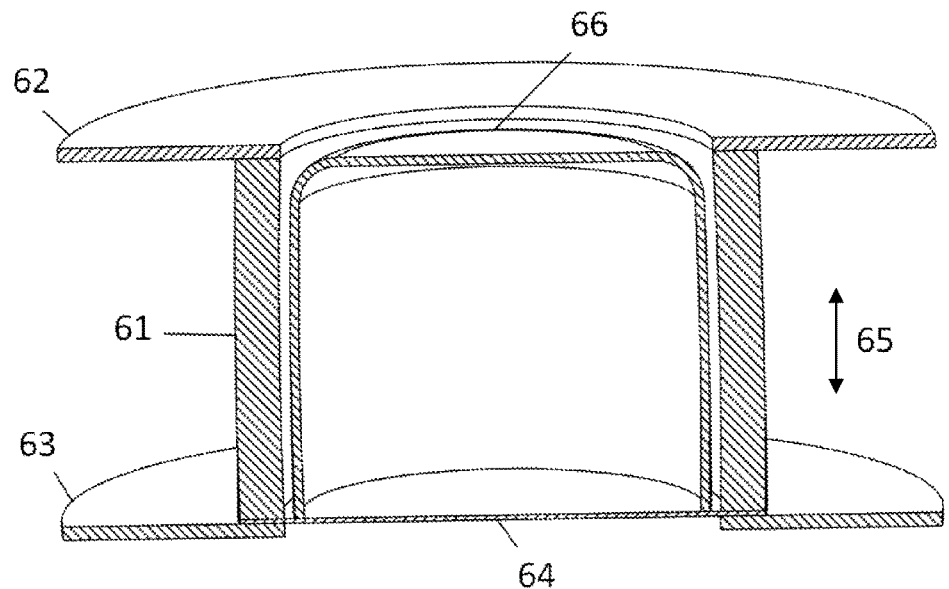
FIG. 6A shows a further mechanical clamping means arrangement for the present invention.
Figure 6B:
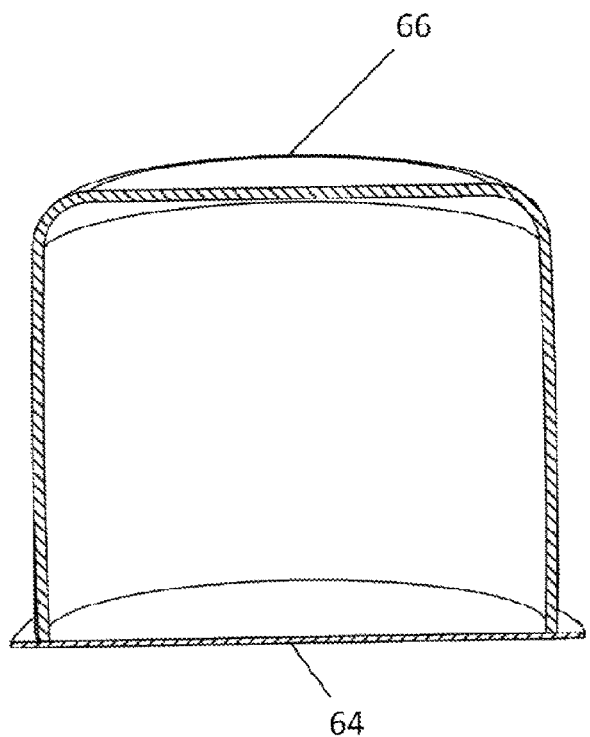
FIG. 6B shows a replaceable dose unit applicable to the clamping means of FIG. 6A.

FIG. 6 shows an alternative arrangement, in which the vibrator element 61 is clamped between opposing clamping members 62 and 63. The membrane 64 is clamped between the vibrator element 61 and one of the opposing clamping members 63. The vibrator element 61 is a longitudinal actuator which creates longitudinal vibrations in the direction of arrow 65 by its expansion and contraction in that direction. In this arrangement, a liquid supply 66, in the form of a dose container is attached to the membrane 64 and is thus free to vibrate with the membrane 64. The walls of the liquid supply 66 may be deformable, such that the membrane 64 can vibrate with the vibrations of the vibrator element 61 without the need to vibrate the whole mass of the liquid supply 66, which can improve the transmission of vibrations to the membrane 64 and improve the general overall performance and efficiency of the device. FIG. 6B shows a membrane 64 and liquid supply 66 for use in the apparatus of FIG. 6A. This comprises a container 66 for carrying a dose of liquid, and a membrane 64 is applied at an opening for releasing liquid from the container, the membrane comprising a plurality of apertures extending through the membrane, for releasing liquid through the apertures. The membrane 64 extends radially outwardly from the container in the plane of the membrane, such that the membrane can be clamped directly to the vibrator member or vibrator element of the apparatus.

Figure 7A:
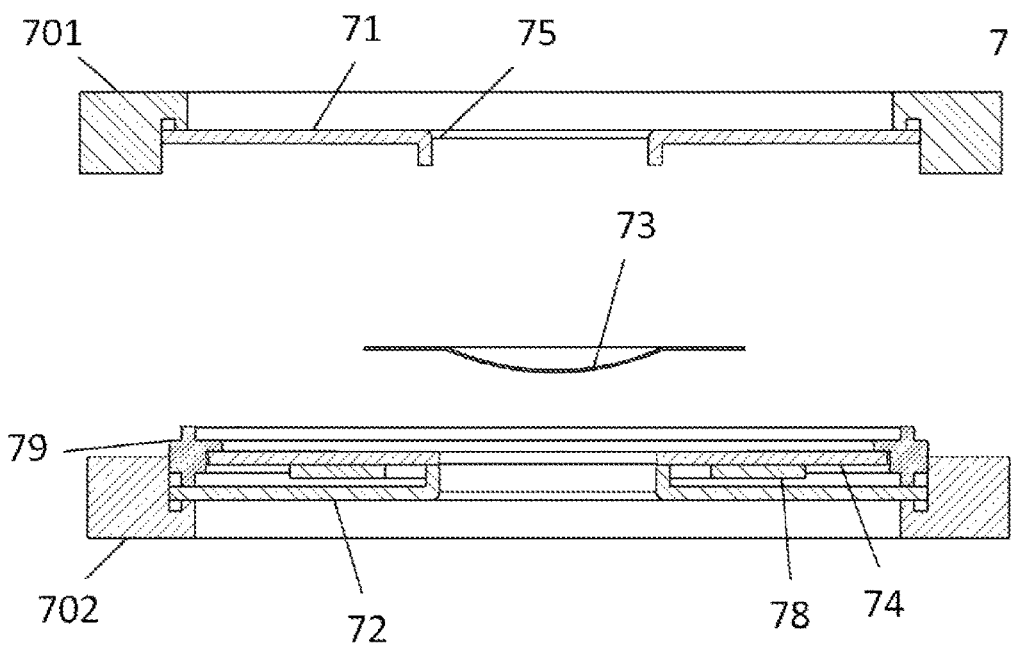
FIGS. 7A and 7B show a further means for mechanical clamping of a membrane and vibrator member of the present invention.

FIG. 7A illustrates an assembly for providing a clamping force in accordance with the present invention. The assembly 7 comprises a first disc spring 71 and a second disc spring 72, which are substantially planar disc-shaped members made from a resilient material. Disc springs 71 and 72 provide resilient biasing members arranged to provide a resilient clamping force toward the outer edge of the membrane 73. In this way a substantially outer portion of the membrane 73 is clamped between the vibrator member 74 and one or more biasing members 71 or 72.

The assembly may therefore comprise first and second resilient biasing members 71 and 72, which are arranged to provide a resilient clamping force in opposition to one another, such that the vibrator member and the membrane are clamped together between the first 71 and second 72 resilient biasing members. Therefore, the biasing members may be disc springs as illustrated in the figures of 7A and 7B and they may comprise a substantially central opening (such that passage may pass through the membrane, which may be located at the central opening of the disc springs.

Either or both of the disc springs 71 and 72 may comprise an annular central section 75 extending away from the planar portion 76 of the disc spring to engage the membrane and/or the vibrator member. This can allow for the spacing between the biasing elements 71 and 72 to provide an accommodating space for the membrane 73 and vibrator member 74, comprising a substrate 77 and vibrator element 78, if necessary.

The assembly may further comprise a spacing member 79, which may be arranged to space apart outer regions of the resilient biasing members 71 and 72. This can allow body control of the magnitude of the clamping force acting on opposing sides of the vibration member 74 and membrane 73 and the system can thus be optimised to provide sufficient clamping force to maintain the membrane 73 in place, while reducing the degree to which the clamping force impacts on the transmission of vibrations from the vibrator and to the membrane.

Figure 7B:
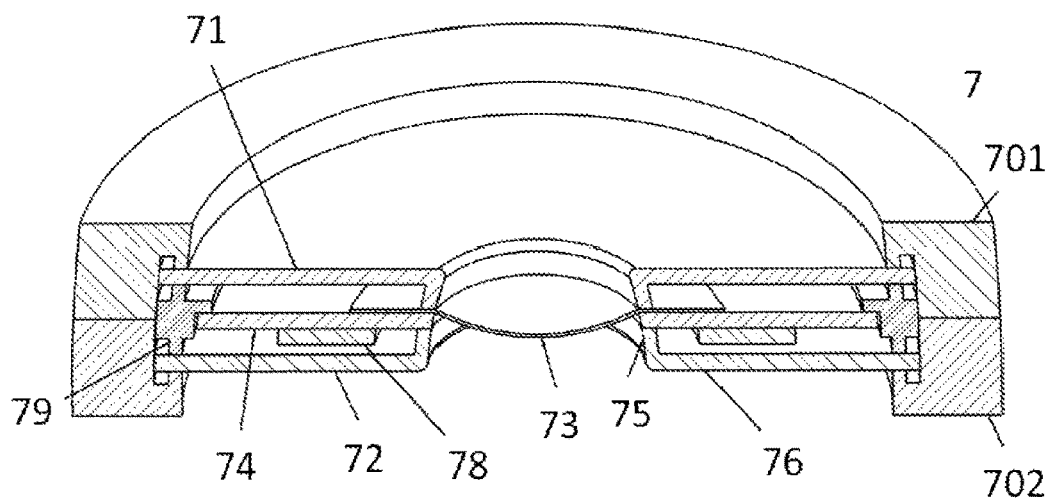

FIG. 7B illustrates a perspective view of an embodiment comprising circular disc springs 71 and 72, separated by a substantially annular spacer 79, to provide spacing in between the disc springs 71 and 72 for the vibrator element 78 and to allow some deformation of the disc springs to provide the required clamping force on the membrane 73 and vibrator member 74. The whole assembly may be maintained in place with supporting members 701 and 702 to provide the required external reaction forces to react to the clamping force provided on the membrane and the vibrator member. These members 701 and 702 may be parts of the apparatus and/or liquid source as appropriate. The provision of a fixed spacing and relative displacement of the disc springs allows a repeatable clamping force to be provided. The assembly can be "opened" as in FIG. 7A for replacement of the membrane 73 and closed again shown in FIG. 7B for use. While open, the spacer 79 may maintain the disc spring 72 and vibrator 74 in place to ease reassembly of the arrangement.

The low mass of the moving parts of the arrangement, when vibration is applied by the vibrator member 74, can provide a high natural frequency of vibration of the assembly, which can improve the efficiency of the device and allow effective transfer of vibrations to the membrane 73. The embodiment of FIG. 7 enables a relatively low inertia, but high spring force for clamping the replaceable membrane in contact with the reusable vibrator member. By providing a fixed displacement of the disc springs, a defined clamping force can be created. The stiffness of the disc springs may be relatively high compared to their mass and by clamping from opposing sides of the vibrator member there is zero net deforming force applied to the vibrator member. This allows the vibration to be transferred more efficiently and effectively to the membrane.

Figure 8:
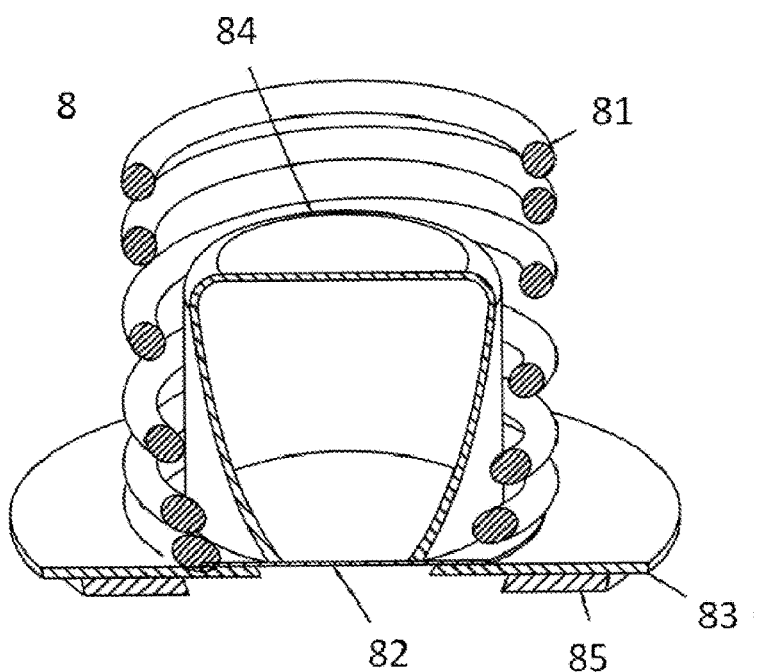
FIG. 8 shows an alternative resilient clamping means for the present invention.
Figure 9A:
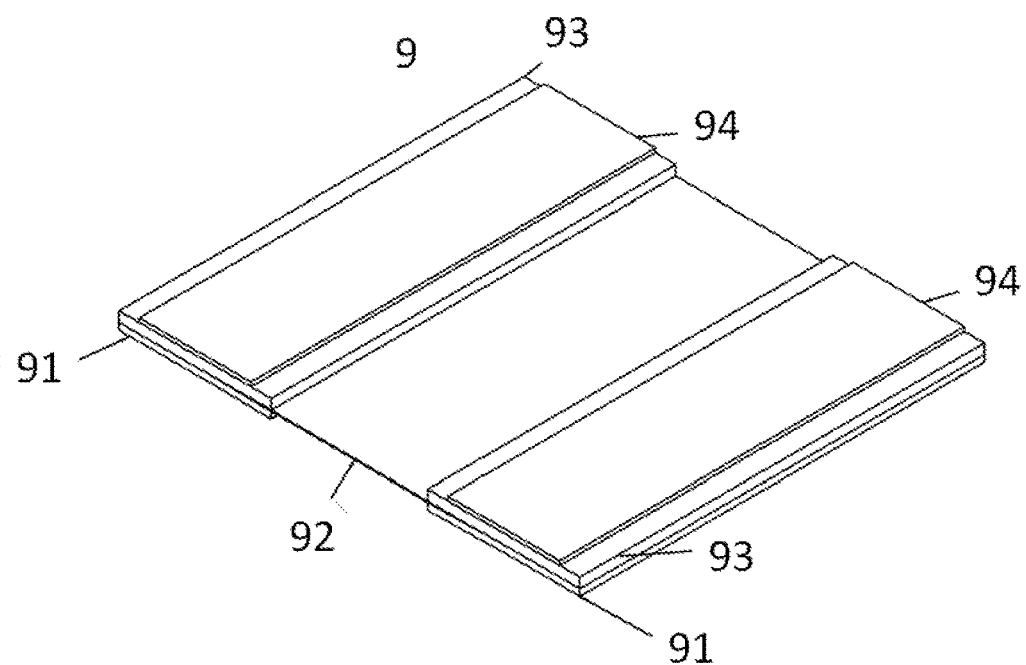
FIGS. 9A and 9B show an alternative clamping means for the present invention.
Figure 9B:
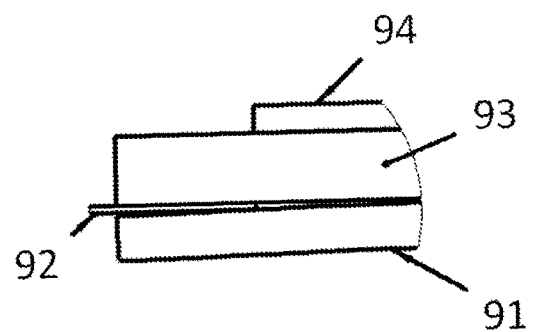

FIG. 8 shows an alternative arrangement 8 in which an alternative, linear, spring, such as a coil spring 81 is provided to clamp the membrane 82 of the arrangement against the substrate 83 and vibrator member 85. The resilient member 81 can provide a clamping force towards an outer edge of the membrane 82, in opposition to a reactive clamping force provided by the substrate 83. An opposing disc spring or coil spring may be provided to balance the force of the first resilient means, coil spring 81, as shown by, for example, element 72 in FIG. 7A. This can help to prevent the clamping forces from inducing bending stresses in the substrate 83, which can dampen its motion and adversely affect transfer of vibration to the membrane 82. A liquid supply 84 may be provided integrally with the membrane 82. A potential drawback of this type of arrangement is that a coil spring 81 as illustrated may have a relatively low natural frequency and as such the clamping force may not be constant during vibration, since the vibration of the vibration member 85 and substrate 83 may be at such a high rate that the coil spring 81 is not able to follow the vibrations to maintain a constant clamping force. However, the solution uses potentially low cost standard parts which can reduce manufacturing costs and complexity and offers an embodiment with reduced sensitivity to component dimensional tolerances FIGS. 9A and 9B illustrate an alternative clamping arrangement 9, in which planar clamping members 91 are provided to clamp a membrane 92 to one or more vibrator members 93. Vibrator members 93 may comprise a substrate and a vibrator element 94. In the figures, the vibrator elements 94 are provided on both lateral sides of the membrane 92. However, it may sufficiently effective to have a vibrator member 93 on only one side of the membrane 92, while the other side provides a clamping function. This therefore provides a simple mechanical clamping arrangement for clamping membrane 92 to vibrator member or members 93. Clamping of the clamping plates 91 to the vibrator members 93 in this embodiment may be implemented by any of the solutions described in relation to the other figures included herein.

Figure 10:
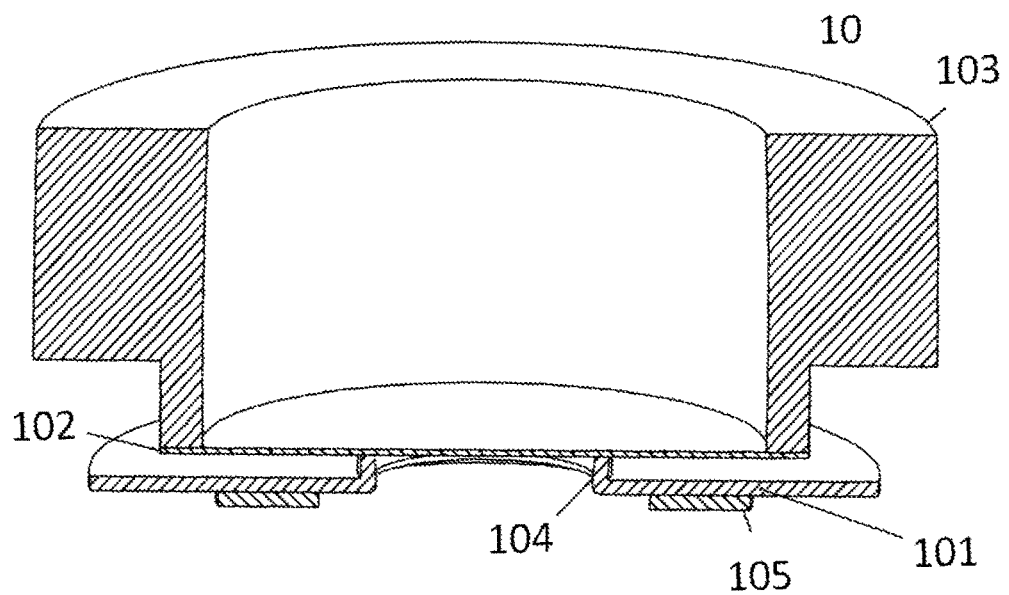
FIG. 10 illustrates an alternative arrangement for clamping of a vibrator member to a membrane according to the present invention.

FIG. 10 illustrates a further alternative arrangement 10 for providing a direct clamping of the vibrator member 101 to the membrane 102. In this embodiment the membrane is retained on a support member 103 substantially at its outer edges, at an outer lateral region of the membrane. The vibrator member 101 comprises a membrane contact portion 104 and a vibrator element 105, which is arranged to transmit vibration to the membrane at a point laterally inward from the outer lateral region. Further elements may be included to directly or indirectly retain the vibrator member 101 in a relatively fixed position relative to the support member 103. As illustrated, the membrane and vibrator member may be substantially circular, although linear or rectanguloid arrangements may also be envisaged. The membrane contact portion 104 may be applied against a membrane 102. Tension is applied by clamping the vibrator member 101 in a position which maintains the membrane 102 under tension, by advancing by a small amount towards the membrane with respect to the un-tensioned position of the membrane 102. The membrane 102 and/or its support member 103 may be permanently attached to, or even integrally formed with, a liquid supply such as a dose container. The membrane contact portion may be a substantially central up-standing part, which extends in a direction substantially perpendicular to the plane of the vibrator member. It may be an upstanding flange and may be substantially annular or circular in form. The arrangement described can result in a very stiff structure, with a low moving mass, and hence the efficient transmission of vibration to the membrane 102 from the vibrator member 101 can be achieved.

Figure 11:
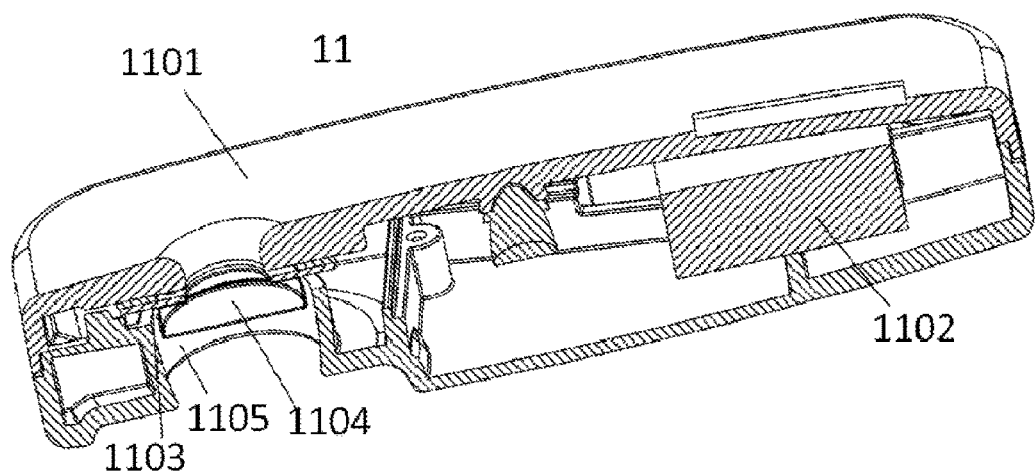
FIG. 11A shows an example of an spray device incorporating the preferred embodiment.
FIG. 11B shows a close up view of the separable mesh unit.
Figure 11:
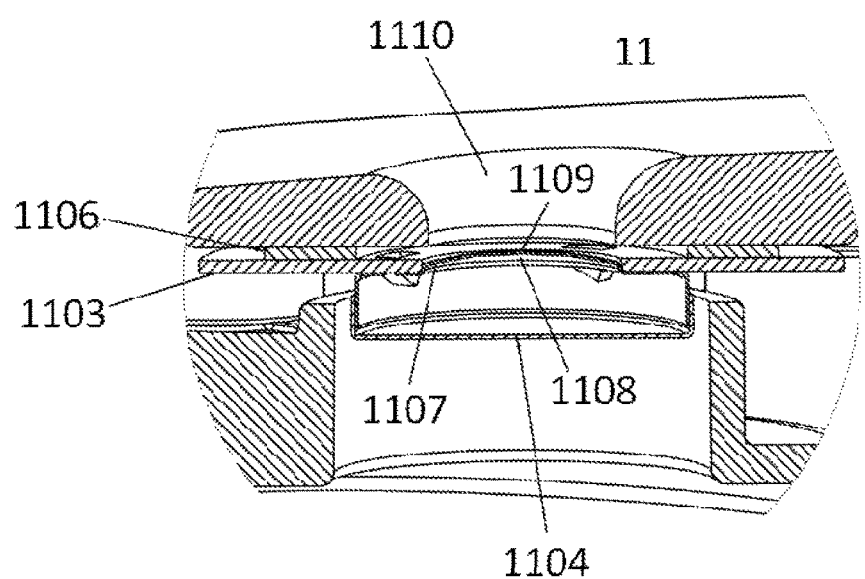

FIGS. 11A and 11B show a spray device 11 incorporating a preferred embodiment of the present invention.

The device includes a body element 1101, in which a power supply 1102 and drive electronics for driving the vibrator member 1103 can be included to control the nebulization of liquid by the device. In the illustrated embodiment, a dose container 1104 is inserted into an opening 1105 in the body 1101 of the device and is engaged with vibrator member 1103 by any of the mechanical clamping means described in relation to the preceding figures. In the particular illustrated embodiment, a rotational engagement means is included to engage a dose container 1104, which is integrated with a membrane of the invention, with the vibrator member 1103.

FIG. 11B shows further detail of the device 11 of FIG. 11A. Here, more detailed features of the arrangement of the vibrator member can be seen, which comprises a substrate 1103 and a vibrator element 1106. A membrane 1107 is held in contact with the substrate 1103 of the vibrator member. As can be seen, a dose container 1104 is integrated with membrane 1107, and can act as a liquid supply to supply liquid to a first side 1108 of the membrane, for ejection from a second side 1109 of the membrane 1107. An opening 1110 is provided in body 11, such that liquid ejected from the membrane 1109 can escape from the spray device into the surrounding atmosphere or toward a user for inhalation, for example.

It can therefore be seen that the integrated dose container 1104 and membrane 1107 can be replaced once the liquid provided within the container 1104 has been used, which may be used up entirely in a single use. The container and integrated membrane can then be disposed of and replaced for the next use, while a maximum number of components are left in the device 11 for use with further container and membrane units.

The invention claimed is:

1. An apparatus for nebulizing a liquid from a liquid supply through a membrane comprising first and second surfaces and a plurality of apertures extending through the membrane from the first surface to the second surface, the apparatus comprising:

a liquid supply receiving area for receiving the liquid supply;

a vibrator member, arranged to vibrate the membrane to eject liquid droplets from the second surface of the membrane on vibration; and mechanical coupling means, arranged to provide a removable mechanical clamping force for clamping the membrane to the vibrator member, wherein the apparatus is arranged for supporting the membrane at an outer lateral region of the membrane and the vibrator member comprises a membrane contact portion arrange to transmit vibration to the membrane at a point laterally inward from the outer lateral region.

2. The apparatus according to claim 1, wherein the vibrator member comprises a vibrator element mounted to a substrate.

3. The apparatus according to claim 2, wherein the mechanical coupling means for clamping is arranged to clamp the membrane directly to the vibrator element.

4. The apparatus according to claim 1, wherein the mechanical coupling means for clamping is arranged to clamp the membrane directly to the vibrator member.

5. The apparatus according to claim 1, wherein the clamping force for clamping of the mechanical coupling means for clamping is balanced within one or both of the vibrator member and the liquid supply.

6. The apparatus according to claim 1, wherein a reacting force that maintains the membrane in vibratory contact with the vibrator member acts locally to an interface between a mesh and the vibrator member.

7. The apparatus according to claim 1, wherein the vibrator member comprises first and second clamping regions having a void therebetween, for allowing liquid to pass through the membrane in the region of the void.

8. The apparatus according to claim 1, wherein the vibrator member and the mechanical coupling means for clamping are arranged to provide a clamping force substantially parallel to the plane of the membrane.

9. The apparatus according to claim 8, wherein at least a part of the clamping force is provided by an interference fit between the membrane and the vibrator member.

10. The apparatus according to claim 8, wherein at least a part of the clamping force is provided by a resilient part of the liquid supply, the resilient part comprising a flexible dose container.

11. The apparatus according to claim 8, wherein at least a part of the clamping force is provided by at least one flexible clamping member of the substrate.

12. The apparatus according to claim 11, wherein the flexible clamping member comprises a membrane contact part and at least one flexible support for biasing the contact part toward the membrane.

13. The apparatus according to claim 8, wherein at least a part of the clamping force is provided by a flexible contact part of the membrane.

14. A membrane for use with an apparatus according to claim 8, the membrane comprising:
   the first and second surfaces and the plurality of apertures extending through the membrane from the first surface to the second surface;
   the apertures located in a substantially planar section of the membrane; and
   a clamping section arranged substantially perpendicular to the planar section to receive the mechanical clamping force in a direction substantially perpendicular to the substantially planar section.

15. The membrane according to claim 14, wherein the clamping section is substantially annular, for receiving a substantially radial clamping force from the mechanical coupling means for clamping.

16. The membrane according to claim 14, further comprising a flexible contact part for providing a clamping force between the membrane and the vibrator member.

17. The apparatus according to claim 1, wherein the membrane is supported at the outer lateral region by a membrane support member and the membrane support member is arranged for direct or indirect connection to the vibrator member, to provide the removable mechanical clamping force.

18. The apparatus according to claim 17, wherein the apparatus is arranged to apply tension to the membrane via the membrane contact portion.

19. The apparatus according to claim 1, wherein the portion of the membrane configured for vibration has a substantially planar substantially circular form and the membrane contact portion is substantially circular.

20. The apparatus according to claim 1, wherein the membrane is permanently attached to the liquid supply.

21. The apparatus according to claim 1, wherein the mechanical coupling means for clamping is arranged to provide a non-magnetic removable mechanical coupling force.

22. A liquid supply for an apparatus comprising a liquid supply receiving area for receiving the liquid supply; a vibrator member, arranged to vibrate a membrane to eject liquid droplets from a second surface of the membrane on vibration; and mechanical coupling means, arranged to provide a removable mechanical clamping force for clamping the membrane to the vibrator member, wherein the apparatus is arranged for supporting the membrane at an outer lateral region of the membrane and the vibrator member comprises a membrane contact portion arrange to transmit vibration to the membrane at a point laterally inward from the outer lateral region, the liquid supply comprising:
   a container for carrying a dose of liquid;
   an opening for releasing the liquid from the container;
   a membrane located at the opening, the membrane comprising first and second surfaces and a plurality of apertures extending through the membrane from the first surface to the second surface for releasing the liquid from the container through the apertures; and
   apparatus engaging means, for engaging the apparatus to locate the membrane at the membrane contact portion of the apparatus.

* * * * *